(12) United States Patent
Paul

(10) Patent No.: US 7,935,360 B2
(45) Date of Patent: May 3, 2011

(54) MEANS FOR BIOLOGICALLY CONTROLLING CRYPTOGAMIC PLANT DISEASES

(75) Inventor: Bernard Paul, Saint Apollinaire (FR)

(73) Assignee: Universite de Bourgogne, Dijon Cedex (FR)

( * ) Notice: Subject to any disclaimer, the term of this patent is extended or adjusted under 35 U.S.C. 154(b) by 569 days.

(21) Appl. No.: 10/520,294

(22) PCT Filed: Jul. 1, 2003

(86) PCT No.: PCT/FR03/02039
§ 371 (c)(1),
(2), (4) Date: May 12, 2005

(87) PCT Pub. No.: WO2004/002227
PCT Pub. Date: Jan. 8, 2004

(65) Prior Publication Data
US 2005/0271629 A1    Dec. 8, 2005

(30) Foreign Application Priority Data
Jul. 1, 2002 (FR) .................................... 02 08212

(51) Int. Cl.
*A01N 25/00* (2006.01)
*A01N 63/00* (2006.01)
*A01N 63/04* (2006.01)
*C12N 1/00* (2006.01)
*C12N 1/20* (2006.01)

(52) U.S. Cl. ... 424/405; 424/93.3; 424/93.4; 424/93.43; 424/93.46; 424/93.51; 435/252.4; 435/252.5; 435/253.5; 435/255.5; 435/837; 435/838; 435/839; 435/874; 435/880; 435/938; 435/945

(58) Field of Classification Search .................. None
See application file for complete search history.

(56) References Cited

U.S. PATENT DOCUMENTS

| 4,981,618 | A | * | 1/1991 | Bruneteau et al. ............. 554/40 |
| 5,270,059 | A | | 12/1993 | Janisiwicz et al. |
| 5,403,583 | A | | 4/1995 | Liu et al. |
| 5,525,132 | A | * | 6/1996 | Shanmuganathan ...... 424/93.51 |
| 6,599,503 | B2 | * | 7/2003 | da Luz .......................... 424/93.3 |

FOREIGN PATENT DOCUMENTS

| FR | 2813166 | 8/2000 |
| WO | WO94/19950 | 9/1994 |

OTHER PUBLICATIONS

PCT International Preliminary Examination Report for International Application No. PCT/FR2003/002039, dated Feb. 2, 2004 (5 p.).
Wilson et al., *Postharvest Biological Control of Penicillium Rots of Citrus With Antagonistic Yeasts and Bacteria*, Database Accession No. PREV198988095325 XP002236920, Abstract, 1989.

* cited by examiner

*Primary Examiner* — Deborah K. Ware
(74) *Attorney, Agent, or Firm* — Conley Rose, P.C.

(57) ABSTRACT

The invention concerns the application of compositions of micro-organisms in biological control of vine cryptogamic diseases. Said composition comprises a mixture of at least one bacterium and at least one yeast, the bacterium or bacteria and the yeast(s) being non-toxic for the plant. The invention also concerns bacterial and yeast strains, as well as biofungicide formulations containing an efficient amount of at least one composition of micro-organisms including in mixture at least one bacterium and one yeast, the bacterium or bacteria and the yeast(s) being non-toxic for the plant, and a composition of filamentous fungi, in particular of the genus *Pichia, Pythium, Trichoderma, Gliocladium, Ampelomyces, Talaromyces, Epicococcum*, combined with an inert carrier. The invention is useful for treating cryptogamic plant diseases, in particular crop plants and vine.

15 Claims, No Drawings

MEANS FOR BIOLOGICALLY CONTROLLING CRYPTOGAMIC PLANT DISEASES

CROSS-REFERENCE TO RELATED APPLICATION

This application is the U.S. National Stage under 35 U.S.C. §371 of International Patent Application No. PCT/FR 03/02039 filed Jul. 1, 2003, which claims priority of French Patent Application No. 0208212 filed Jul. 1, 2002.

The invention is aimed at means, namely compositions and methods, for biologically controlling cryptogamic plant diseases, i.e. caused by pathogenic fungi.

Biological control, i.e. the use of living microorganisms to combat plant diseases, arouses much interest given the growing problems posed by the use of chemical fungicides in agriculture. Polluted water tables, contaminated soils, and the resistance of pathogenic fungi to the fungicides are all challenges to be overcome by modern agriculture.

In the field of viticulture for example, it is necessary to produce ever higher quality wines and to reduce the pollution caused by the intensive use of chemicals.

Bacteria, such as *Bacillus thuringiensis*, or fungi, such as *Beauveria* or *Endothia* have already been proposed as biological control means.

Now, the inventors have been able to develop highly effective non-toxic means by using microorganisms in a mixture to control cryptogamic vine diseases. Such mixtures not only act in synergy in the desired biological control, but also advantageously have an eliciting effect.

Moreover, it has been observed that particular mixtures of microorganisms were particularly effective for the treatment of cryptogamic plant diseases in general.

The purpose of the invention is therefore the use of microorganisms in the biological control of cryptogamic vine diseases.

It also aims to provide new compositions of microorganisms and their use as means for biologically controlling cryptogamic plant diseases, more specifically cryptogamic diseases in crop plants.

The use of compositions of microorganisms in the biological control of cryptogamic vine diseases is characterized in that it comprises in a mixture at least one bacterium and at least one yeast, the bacterium or bacteria and the yeast or yeasts being non-toxic to plants.

Advantageously, the bacterium or bacteria are chosen from the *Bacillus, Pseudomonas, Serratia* or *Streptomiyces* groups.

This bacterium or bacteria is in particular from the *Bacillus megaterium* species, and in particular from the strain deposited on the 20 Jun. 2002 at the CNCM, 25 rue du Dr. Roux, 75724 Paris Cedex 15, under No. I-2897 and bacterium or bacteria from the Bacillus subtilis species deposited on the 20$^{th}$ June at the same institution under No. I-2940.

The yeast or yeasts of the compositions of the invention are advantageously of the Debaryomyces or *Pichia* genus. In particular it is the yeast of the Debaryomyces genus deposited on the 20 June at the CNCM under No. I-2896.

In particular the invention relates to, as newly isolated products, the *Bacillus megaterium* (BP B-01) strain deposited on the 20 Jun. 2002 at the CNCM, 25 rue du Dr. Roux, 75724 Paris Cedex 15, under No. I-2897 and the *Bacillus subtilis* (BP B-10) strain deposited at the CNCM on the 20 Jun. 2002 under No. I-2940.

The invention is also relates to, as a newly isolated product, the yeast of the *Debaryomyces* (BP Y-01) genus deposited on the 20 Jun. 2002 at the CNCM under No. I-2896.

The strains of bacteria and yeast of the invention are advantageously selected from microorganisms from the soil or taken from the plant to be treated. Therefore they do not disturb the biological balance of the ecosystem because they originate from it.

The compositions of these microorganisms allow treatment of the main plant fungus diseases and are therefore particularly suitable for developing biofungicide preparations.

Preparations of the invention are characterized in that they contain an effective quantity of at least one composition of microorganisms comprising in a mixture at least one bacteria and at least one yeast, the bacterium or bacteria and the yeast or yeasts being non-toxic to the plant, as well as a composition of filamentous fungi, in particular of the *Pichia; Pythium, Trichoderma, Gliocladium, Ampelomyces, Talaromyces, Epicococcum* genus in combination with an inert vehicle.

The vehicle used is in particular able to ensure good dispersion and adhesion of the microorganisms on the aerial part of the plant.

Preferred biofungicide preparations are characterized in that they contain an effective quantity of the bacterial strains and of the strain of yeast deposited at the CNCM, as defined above. Preferably, the biofungicide preparations of the invention are characterized by concentrations of yeasts of 0.5 to $0.75 \times 10^{10}$ and of bacteria of 0.30 to $0.50 \times 10^{10}$.

These preparations have a broad spectrum of effectiveness against pathogenic fungi and are advantageously used for the treatment of cryptogamic diseases in plants, in particular in crop plants, in particular in the aerial parts for example vine, tomato, strawberry, wheat, potato, tobacco, sugar cane, corn, rice, fruit-trees, in tubers for example potatoes or beet.

The effectiveness was also noted in particular in market-garden plants.

They are used for example in the treatment of powdery mildew, blue mould, and *Botrytis* of the vine, as well as wood diseases (esca or eutypa).

These preparations also have the advantage of having an eliciting effect which causes activation of the natural defences of the plant against aggressors of fungal origin.

The treatments are carried out in particular by spraying on the aerial parts with preparations containing the bacterium or bacteria and the yeast or yeasts, with quantities which are adjustable according to the pathogen pressure. Suitable preparations contain for example said bacteria and yeasts in a ratio of approximately 50/50%.

It will be noted that the application of these treatments does not require any change of equipment on the part of the user.

According to another provision of the invention, the treatment is completed, if appropriate, using a composition of fungi, more specifically of filamentous fungi, in particular of the *Pythium, Trichoderma, Gliocladium, Ampelomyces, Talaromyces, Epicococcum* genus.

After the application, the strains of the preparation remain on the plant for a few days only before dying and decomposing. Their presence in the soil is not greater than a level normally encountered and is non-existent below thirty centimetres in depth.

These mixtures of microorganisms therefore do not produce any new form of pollution.

The invention also aims to take advantage of the eliciting effect of the mixtures of microorganisms of the invention to produce compounds of interest, such as resveratrol, a molecule having in particular a protective effect on the cardiac system, or also pterostilbene, in higher quantities than those produced by the vine after elicitation such as produced by *Botrytis*.

The invention is thus aimed at a method for the production of resveratrol and/or pterostilbene, comprising the application to a plant, in particular vines, of a composition of microorganisms as defined above, and the recovery of resveratrol and/or pterostilbene for example by extraction.

Resveratrol can be used for the production of medicaments in particular for cardiovascular purposes, in cosmetology or as a nutriceutical. Pterostilbene can be used as an antifungal.

Other characteristics and advantages of the invention will become apparent from the following examples given by way of illustration of the invention and with reference to the single FIGURE which presents the production of resveratrol with different combinations of bacteria and/or yeasts and/or fungi.

EXAMPLE I

Isolation and Culture of the Strain of Bacteria BP B01 and of Yeast BP Y01

The isolation takes place as follows:

The two microorganisms are cultured on a solid PDA (potato dextrose agar) nutrient medium. The two microorganisms are seeded separately in 20 litre fermenters containing PDB (potato dextrose broth). The yeasts are cultured at 28° C. and the bacteria at 37° C. The microorganisms thus prepared are centrifuged and the pellet of bacteria and yeasts is recovered separately in sterile distilled water. When the plant is treated, the two microorganisms are mixed. The vineyard undergoes three treatments per month, from April to August, thus a total of 10 to 12 treatments with the mixture of the invention for the season. The product prepared by fermentation is used for the whole season, each litre containing from $0.5$-$0.75 \times 10^{10}$ for the yeasts and $0.30$-$0.50 \times 10^{10}$ for the bacteria, at a rate of 1 litre per vine trunk.

Characterization of the Genomic DNA of BP B01 and BP B10

The isolation of the genomic DNA of BP B01 and of BP B10, as well as the amplification of their ITS region, between the 16S and 23S genes was carried out according to Chen. W, Schneider R. W, and Hoy J. W. 1992, Phytopathology, 82, p. 1234-1244. The corresponding sequences SEQ ID No. 1 and SEQ ID No. 3 were deposited at GENBANK (access No.s AY 125961 and AY 157575 respectively).

The yeast BP Y01 was isolated from grapes from different vineyards of the Burgundy region.

The genomic DNA of BP Y01 was isolated and the ITS region, between the 18S and 28S genes was amplified according to the above methods.

The ITS1 fragment is located between the 18S and 5,8 S genes, while ITS2 is located between the 5,8 S and 28 S genes. The sequence SEQ ID No. 2 was deposited at GENBANK (access No. AY 125962).

Results of Biological Control on Chardonnay Grapes in 1999 and 2000 at the Centre Expérimental de Marsannay-La-Côte, France (Université de Bourgogne)

| Year: 1999 | Results |
| --- | --- |
| Number of trunks | 450 |
| Non-treated controls | 10 |
| Number of treatments | 15 |

-continued

| | |
| --- | --- |
| Type of inoculum | Bacteria + yeasts |
| Protection | 39 diseased trunks (blue mould), O *Botrytis* |
| Controls | Blue mould then *Botrytis* on all the trunks, chemical intervention |

| Year: 2000 | Results |
| --- | --- |
| Number of trunks | 241 |
| Number of treatments | 14 |
| Type of inoculum | Bacteria + yeasts |
| Protection | 27 diseased trunks (blue mould), O *Botrytis* |
| Controls | Blue mould then *Botrytis* on all the trunks |

Results of Biological Control on Pinot-Noir Grapes in 2000 and 2001 at the Centre Expérimental de Marsannay-La-Côte, France (Université de Bourgogne)

| Year: 2000 | Results |
| --- | --- |
| Number of trunks | 120 |
| Non-treated controls | 13 |
| Number of treatments | 14 |
| Type of inoculum | Bacteria + yeasts |
| Controls | Blue mould then *Botrytis* on all the trunks |
| Protection | 11 diseased trunks (blue mould), O *Botrytis* |

| Year: 2001 | Results |
| --- | --- |
| Number of trunks | 614 |
| Number of treatments | 13 |
| Chemical treatment | 02 |
| Non-treated controls | 13 |
| Type of inoculum | Bacteria + yeasts |
| Controls | Blue mould + *Botrytis* on all the trunks |
| Protection | 53 diseased trunks (blue mould), a few bunches infected with *Botrytis* |
| Yield | 1.18 kg of grapes per trunk instead of 1.2–1.5 kg |

Generally, in addition to the fungicide and eliciting effect of the preparations used, an improvement in the quality of the grape harvest is noted. In particular an increase in the concentration of sugar which allows chaptalization to be reduced or avoided is observed. Moreover, the level of resveratrol is increased. Finally, the levels of tannin and anthocyanins increase, which gives the wine greater fullness and brighter colour.

The results relating to the increase of resveratrol are illustrated by the histogram of the single FIGURE which gives in ug/gm of fresh weight the production of resveratrol on the $3^{rd}$ day after addition respectively of: BP Y01 (yeast deposited at the CNCM); BP B01 (bacteria deposited at the CNCM); BC 03 (botrytis cinerea); BP Y01+B C03; BPB 01+B C03; BP Y01+BP B01; BP B01+BP Y01+B C03.

Examination of this histogram shows that the formation of resveratrol increases when the yeast/bacteria mixture of the invention is added to the *Botrytis* fungus.

Taking into account all of these properties, the compositions used as fungicide preparations, according to the invention, constitute a particularly satisfactory response to the fungicide problems which growers, in particular wine growers are facing and to the need to reduce pollution caused by agriculture by constituting substitutes to chemical products.

The invention claimed is:

1. A method for biologically controlling a cryptogamic vine disease, comprising applying to a vine having said cryptogamic vine disease an effective amount of a mixture consisting of a biologically pure bacterium, wherein said biologically pure bacterium is *Bacillus megaterium* strain CNCM Deposit No. 1-2897, a biologically pure yeast and an inert vehicle, each of said bacterium and said yeast in the mixture being non-toxic to the vine to treat said disease.

2. The method according to claim 1, wherein said yeast is from a genus selected from the group consisting of *Debaryomyces* and *Pichia*.

3. The method of claim 1, said mixture containing per liter a yeast concentration of from 0.5 to $0.75 \times 10^{10}$ of said yeast and a bacterial concentration of from 0.30 to $0.50 \times 10^{10}$ of said bacterium.

4. The method of claim 1, wherein said cryptogamic vine disease is powdery mildew, blue mould or Botrytis.

5. The method of claim 1, wherein said applying includes spraying said vine with said mixture having an approximately 50/50 ratio of said bacterium to said yeast.

6. A method for biologically controlling a cryptogamic vine disease, comprising applying to a vine having said cryptogamic vine disease an effective amount of a mixture consisting of a biologically pure bacterium, wherein said biologically pure bacterium *Bacillus subtilis* CNCM Deposit No. 1-2940, a biologically pure yeast and an inert vehicle, each of said bacterium and said yeast in the mixture being non-toxic to the vine to treat said disease.

7. The method according to claim 6, wherein said yeast is from a genus selected from the group consisting of *Debaryomyces* and *Pichia*.

8. The method of claim 6, said mixture containing per liter a yeast concentration of from 0.5 to $0.75 \times 10^{10}$ of said yeast and a bacterial concentration of from 0.30 to $0.50 \times 10^{10}$ of said bacterium.

9. The method of claim 6, wherein said cryptogamic vine disease is powdery mildew, blue mould or *Botrytis*.

10. The method of claim 6, wherein said applying includes spraying said vine with said mixture having an approximately 50/50 ratio of said bacterium to said yeast.

11. A method for biologically controlling a cryptogamic vine disease, comprising applying to a vine having said cryptogamic vine disease an effective amount of a mixture consisting of a biologically pure bacterium, a biologically pure yeast, wherein said biologically pure yeast is *Debaryomyces* CNCM Deposit No. 1-2896, and an inert vehicle, each of said bacterium and said yeast in the mixture being non-toxic to the vine to treat said disease, and wherein said bacterium is from a genus selected from the group consisting of *Bacillus, Pseudomonas, Serratia* and *Streptomyces*.

12. The method of claim 11, said mixture containing per liter a yeast concentration of from 0.5 to $0.75 \times 10^{10}$ of said yeast and a bacterial concentration of from 0.30 to $0.50 \times 10^{10}$ of said bacterium.

13. The method of claim 11, wherein said cryptogamic vine disease is powdery mildew, blue mould or *Botrytis*.

14. The method of claim 11, wherein said applying includes spraying said vine with said mixture having an approximately 50/50 ratio of said bacterium to said yeast.

15. A method for biologically controlling a cryptogamic vine disease, comprising applying to a vine having said cryptogamic vine disease an effective amount of a mixture consisting of at least one biologically pure bacterium selected from the group consisting of *Bacillus megaterium* strain CNCM Deposit No. 1-2897 and *Bacillus subtilis* CNCM Deposit No. 1-2940, at least one biologically pure yeast, filamentous fungi selected from the group consisting of *Pichia, Pythium, Trichoderma, Gliocladium, Ampelomyces, Talaromyces*, and *Epicoccum*, and an inert vehicle, each said bacterium and each said yeast in the mixture being non-toxic to the vine the to treat said disease.

* * * * *

SEQUENCE LISTING

<160> NUMBER OF SEQ ID NOS: 3

<210> SEQ ID NO 1
<211> LENGTH: 335
<212> TYPE: DNA
<213> ORGANISM: Bacillus megaterium

<400> SEQUENCE: 1

```
acgtttggac actttgttca gttttgagag agtaatctct caattataga aagcacacta      60
ctttcttctt atttaataag aagaatattg gctgcgattg ttctttgaaa actagataac     120
agtcattgct gaggaaaagt gaaacttttc tttaatcaaa ccaataaata acacaacagt     180
atgttgtacc atttattcgc taatggttaa gttagaaagg gcgcacggtg aatgccttgg     240
cactaggagc cgatgaagga cgggactaac accgatgtgc ttcggggagc tgtaagtgag     300
ctttgatccg gagatttccg aatggggaaa cccgc                                335
```

<210> SEQ ID NO 2
<211> LENGTH: 581
<212> TYPE: DNA
<213> ORGANISM: Debaryomyces hansenii

<400> SEQUENCE: 2

```
ggatcattac agtattcttt tgccagcgct taactgcgcg gcgaaaaacc ttacacacag      60 tgtcttttg atacagaact cttgctttgg tttggcctag agataggttg ggccagaggt     120
ttaacaaaac acaatttaat tatttttaca gttagtcaaa ttttgaatta atcttcaaaa     180
ctttcaacaa cggatctctt ggttctcgca tcgatgaaga acgcagcgaa atgcgataag     240
taatatgaat tgcagatttt cgtgaatcat cgaatctttg aacgcacatt gcgccctctg     300
gtattccaga gggcatgcct gtttgagcgt catttctctc tcaaaccccc gggtttggta     360
ttgagtgata ctcttagtcg gactaggcgt ttgcttgaaa agtattggca tgggtagtac     420
tagatagtgc tgtcgacctc tcaatgtatt aggtttatcc aactcgttga atggtgtggc     480
gggatatttc tggtattgtt ggcccggcct tacaacaacc aaacaagttt gacctcaaat     540
caggtaggaa tacccgctga acttaagcat atcaataagc g                         581
```

<210> SEQ ID NO 3
<211> LENGTH: 312
<212> TYPE: DNA
<213> ORGANISM: Bacillus subtilis

<400> SEQUENCE: 3

```
ggatcccctc ctttctaagg attttaacgg aatataagac cttgggtctt ataaacagaa      60
cgttccctgt cttgtttagt tttgaaggat cattcgattc ttcgagatgt tgttctttga     120
aaactagata acagaagtaa ttcacattca attagtaatg caagatatca cgtagtgatt     180 cttttttaacg gttaagttag aaagggcgca cggtggatgc cttggcacta ggagccgatg     240
aaggacggga cgaacaccga tatgcttcgg ggagctgtaa gcaagctttg atccggagat     300
ttccgaatgg gg                                                         312
```